United States Patent [19]

Cry et al.

[11] Patent Number: 4,899,047
[45] Date of Patent: Feb. 6, 1990

[54] METHOD AND APPARATUS FOR SELECTIVELY DETECTING ONE OF TWO IMMISCIBLE LIQUIDS IN THE PRESENCE OF THE OTHER LIQUID

[75] Inventors: John W. Cry; Randy R. Kirkham; John F. McBride; Carver S. Simmons; Glendon W. Gee, all of Richland, Wash.

[73] Assignee: Battelle Memorial Institute, Richland, Wash.

[21] Appl. No.: 210,874

[22] Filed: Jun. 24, 1988

[51] Int. Cl.$^4$ .................................. H01J 5/16
[52] U.S. Cl. ............................ 250/227; 73/73
[58] Field of Search ............... 250/573, 574, 576, 227, 250/338.5, 231; 356/434, 436; 73/73

[56] References Cited

U.S. PATENT DOCUMENTS

| | | | |
|---|---|---|---|
| 3,867,837 | 2/1975 | Malin | 73/73 |
| 4,221,962 | 9/1980 | Black et al. | 73/73 |
| 4,634,856 | 1/1987 | Kirkham | 73/73 |
| 4,655,076 | 4/1987 | Weihe et al. | 73/73 |

FOREIGN PATENT DOCUMENTS 0126600 11/1984 European Pat. Off. .
8605589 9/1986 European Pat. Off. .

Primary Examiner—David C. Nelms
Assistant Examiner—K. Shami
Attorney, Agent, or Firm—Dellett, Smith-Hill and Bedell

[57] ABSTRACT

Oil is detected in the presence of water by placing a translucent, porous body of hydrophobic material in contact with the oil and water and detecting the amount by which light incident on the body is attenuated on propagation through the body.

16 Claims, 2 Drawing Sheets ed 4,899,047

METHOD AND APPARATUS FOR SELECTIVELY DETECTING ONE OF TWO IMMISCIBLE LIQUIDS IN THE PRESENCE OF THE OTHER LIQUID

BACKGROUND OF THE INVENTION

This invention was made with support of the U.S. government under contract No. DE-AC06-76RLO 1830, awarded by the U.S. Department of Energy. The U.S. government has certain rights in the invention.

This invention relates to a method and apparatus for selectively detecting the presence of one of two immiscible liquids in the presence of the other liquid. In this description, and in the claims, reference to liquids being immiscible is intended to include not only liquids that are completely immiscible but also liquids that are partially immiscible.

When an organic liquid escapes from a container, e.g. gasoline escapes from a leaky, below-ground tank, the liquid may enter the soil and percolate downwards through the unsaturated zone of the soil above the water table. It is desirable to be able to detect organic liquids in the soil in order to enable steps to be taken to prevent contamination of the ground water.

Known methods of detecting water in soil are described in A. Klute (ed), Methods of Soil Analysis, part 1—Physical and Mineralogical Methods, 2nd edition, American Society of Agronomy, 1986. One of the known methods involves use of a block of porous material formed with an internal cavity. The block is saturated with water and is placed in the soil. The water permeates into the soil, reducing the pressure inside the cavity, until an equilibrium is reached. The equilibrium pressure inside the cavity is a measure of the concentration of water in the soil before the block was placed in the soil. This method is subject to disadvantage, in that it is not readily applicable to in situ measurements. Moreover, it is not applicable to measurement of very low concentrations, since at low concentrations the pressure inside the cavity becomes sufficiently low for the water to vaporize, preventing measurement of the pressure inside the cavity.

R. S. Alessi and L. Prunty, Soil Water Determination Using Fiber Optics, Soil Sci. Soc. Am. J. 50, 860, 1986, describes a method of measuring the concentration of water in porous material, e.g. unsaturated soil, by placing a glass rod in the porous material. The rod is bent through a critical angle such that the light lost from the rod depends on the amount of water touching its surface which in turn depends on the packing of porous material around the rod.

U.S. Pat. No. 4,634,856 issued Jan. 6, 1987 (Kirkham) describes a method of measuring moisture content of soil by detecting light reflected from the soil.

Methods of detecting organic liquids in soil are described in Report PB 87-212346 published by the U.S. Department of Commerce, National Technical Information Service. These methods include detecting the vapors of the organic liquids, and use of dyes that change color on contacting organic liquids.

Summary of the Invention

A preferred embodiment of the invention in its first aspect is apparatus for detecting a first of two immiscible liquids in the presence of the second liquid, comprising a translucent, porous body that absorbs the first liquid in preference to the second liquid, and means for detecting the amount by which light incident on the body is attenuated on propagation through the body.

A preferred embodiment of the present invention in its second aspect is a method for detecting a first of two immiscible liquids in the presence of the second liquid, comprising providing a translucent, porous body that absorbs the first liquid in preference to the second liquid, placing the body in contact with the first and second liquids, and detecting the amount by which light incident on the body is attenuated on propagation through the body.

A preferred embodiment of the present invention in its third aspect is a method for detecting the degree to which a translucent, porous body is saturated with liquid, comprising the steps of illuminating the body and detecting the amount by which light is attenuated on propagation through the body.

The word "translucent" is used herein to describe the property of being able to transmit light, and when applied to a porous body is intended to cover a body that diffuses light transmitted by the body.

BRIEF DESCRIPTION OF THE DRAWINGS

For a better understanding of the invention, and to show how the same may be carried into effect, reference will now be made, by way of example, to the accompanying drawings in which.

In the several figures, like reference numerals designate corresponding elements.

DETAILED DESCRIPTION

Figure 1:
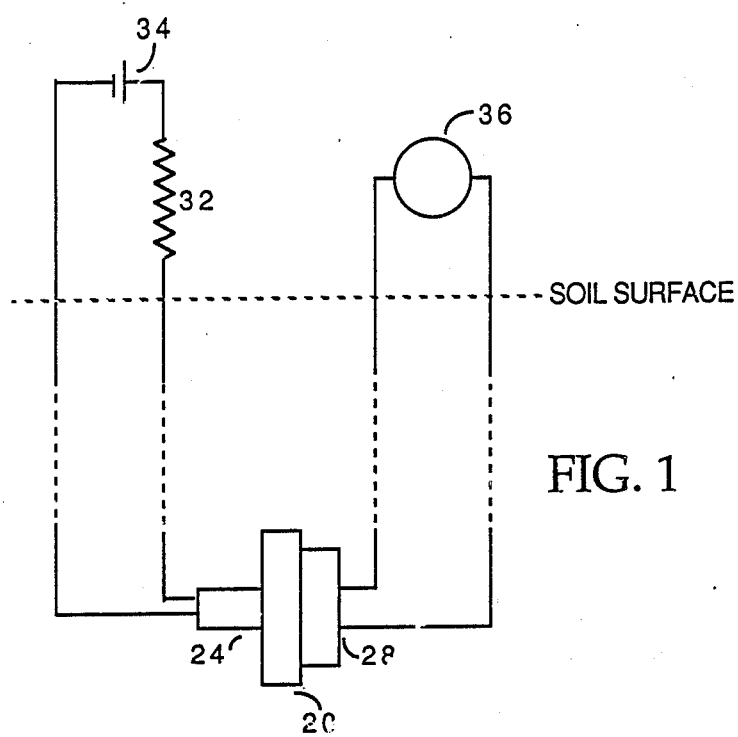
FIG. 1 is a schematic view illustrating apparatus for detecting an organic liquid in soil.

A fritted glass disk, 4 mm thick and 6 cm in diameter was placed between a light-emitting diode (LED) that emits visible light and a CdS light detector. The LED and the detector were held in contact with opposite faces of the disk by a spring clip. The electrical resistance of the detector was found to be strongly dependent on the water content of the disk. The resistance of the detector when the disk was fully saturated with water was about 9,000 ohm, as compared with 1.5 Megohm when the disk was nearly dry. The resistance decreased substantially linearly as the degree of saturation increased from about 50% to 100%.

In an experiment that was conducted with a 2 mm thick fritted glass disk, an LED that emits light in the infra-red region, and a silicon diode connected to a 5,000 ohm load resistor, the change in voltage developed across the resistor was about 140 mv for a change in saturation of the disk from 0% to 100%.

In a further experiment, a strip of Teflon (registered trademark) filter paper was used in lieu of the 2 mm fritted glass disk of the previous experiment. The voltage developed across the load resistor increased by 31 mv as the filter paper passed from the dry state to a state in which it was saturated with oil.

These experiments demonstrate that the intensity with which light is transmitted by a translucent, porous body that is dimensionally stable with respect to the direction of the transmission depends strongly on the degree to which the pore space of the body is filled with translucent liquid. Therefore, a fritted glass disk may be used to detect water in porous, unsaturated soil, since water will be adsorbed on the surface of the disk and absorbed into the pores in the interior of the disk. If an organic liquid that is not miscible with water, such as an oil, is present in the unsaturated soil, the organic liquid will wet the water surface and displace air from the pores. If the soil were saturated, the pores would be filled with water, to the exclusion of the organic liquid. If a fritted polyethylene disk is placed in unsaturated soil containing both an oil and water, the oil and not the water will be adsorbed on the surface of the polyethylene and absorbed into the pores in the interior of the disk.

If a translucent, porous body of hydrophilic material and a translucent, porous body of hydrophobic material are placed in unsaturated soil containing both water and a transparent organic liquid that is not miscible with water, water present in the soil enters the pores of the body of hydrophilic material, but not the pores of the body of hydrophobic material, and the organic liquid enters the pores of both the body of hydrophobic material and the body of hydrophilic material. An equilibrium is reached with respect to water when the capillary pressure in the body of hydrophilic material is equal to the capillary pressure of the water in the soil, and similarly an equilibrium is reached with respect to the organic liquid when the capillary pressure of the organic liquid in the bodies of hydrophobic and hydrophilic material is equal to the capillary pressure of the organic liquid in the soil. Consequently, the capillary pressure of the organic liquid can be inferred from the light transmission of the body of hydrophobic material and the capillary pressure of water can be inferred from the light transmission of the body of a hydrophilic material and the capillary pressure of the organic liquid. The capillary pressure of a liquid in the soil determines how the liquid moves through the soil.

The apparatus illustrated in FIG. 1 comprises a plate 20 of porous fritted polyethylene, which is available from Porex of Fairburn, Ga. The plate is approximately 4 mm thick and 1 cm square. An LED 24 that emits visible light is cemented to one square face of the plate, and a CdS light detector 28 is cemented to its other square face. A suitable cement is silicon rubber. The LED 24 is connected in series with a ballast resistor 32 between the terminals of a battery 34, and the terminals of the light detector 28 are connected to an ohm meter 36. The assembly of the plate 20, the LED 24 and the CdS detector 28 forms a liquid detection cell, which is placed in the soil. The battery 34 and the ohm meter 36 remain above ground. The plate 20 absorbs organic liquids, such as gasoline and oil, that are present in the soil. The amount of organic liquids absorbed by the plate depends on the concentration of those organic liquids in the soil and determines the intensity with which light emitted by the LED 24 is received by the detector 28. Accordingly, the concentration of organic liquids in the soil can be readily monitored by observing the resistance value indicated by the ohm meter 36.

The apparatus shown in FIG. 2 requires only two conductors running from above ground to below ground, instead of four as in the case of the FIG. 1 apparatus. The FIG. 2 apparatus provides a voltage output signal and has increased sensitivity at high degrees of saturation, because as the resistance of the detector decreases, the current through the LED rises so that the detector is illuminated more strongly, and this in turn further reduces the resistance of the detector.

Figure 3:
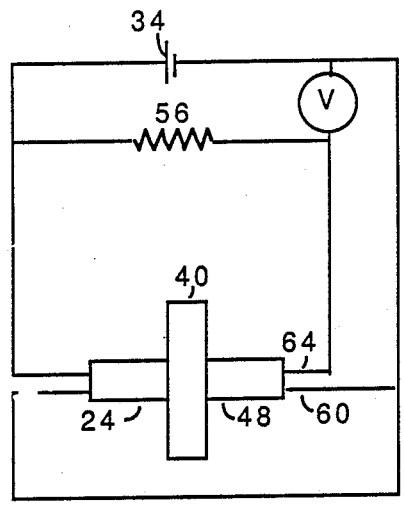

The apparatus illustrated in FIG. 3 comprises a disk 40 of translucent, porous material. The LED 24 is secured to one surface of the disk 40, and a phototransistor 48 is secured to the other surface of the disk. The terminals of the LED 24 are connected to the battery 34. The negative terminal of the battery is connected directly to one terminal 60 of the transistor 48, and the positive terminal of the battery is connected to the other terminal 64 of the transistor 48 through a load resistor 56. The transistor supplies a current of which the magnitude depends on the intensity with which the transistor is illuminated. A voltage signal proportional to this current is developed between the two terminals 60 and 64. The apparatus shown in FIG. 3 may therefore be used to sense the concentration of water in the soil if the disk is made of fritted glass and the concentration of water-immiscible organic liquids if the disk is made of fritted polyethylene.

Uncoated filter paper made from cellulosic fibers is hydrophilic and may be used in lieu of the disk of the detection cell of FIG. 3. However, if there is no water in the soil but the soil contains organic liquid, the organic liquid will be absorbed into the pores of the disk 40 or uncoated filter paper and therefore an indication that the disk 40 or the filter paper contains liquid is ambiguous as to whether the liquid is water or an organic liquid. Filter paper made from cellulosic fibers and having a coating of hydrophobic material is commercially available. By use of two detection cells, one employing uncoated filter paper and the other employing filter paper coated with hydrophobic material, it is possible to determine the capillary pressure both of water and of organic liquids that are not immiscible with water.

Figure 2:
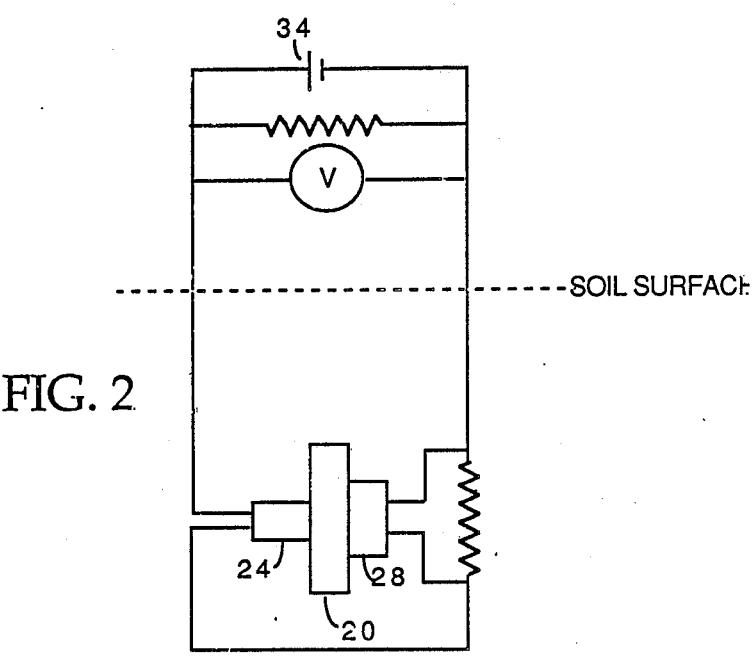
FIGS. 2, 3 and 4 illustrate respective modifications of the FIG. 1 apparatus.
Figure 4:
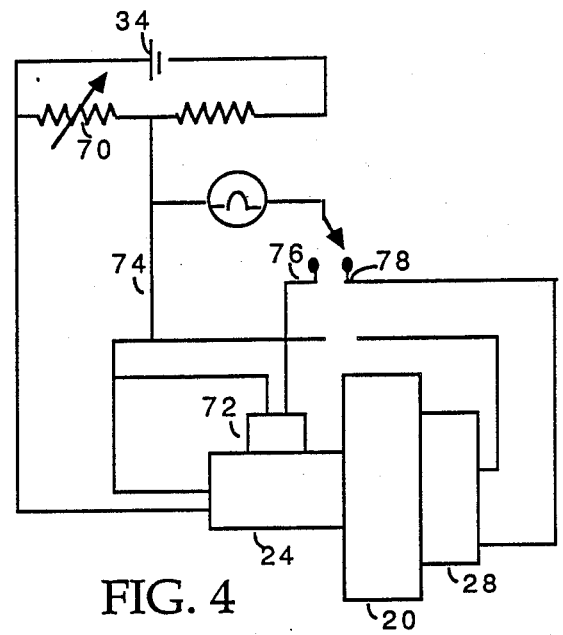

FIG. 4 illustrates a still further modification of the FIG. 2 apparatus. In FIG. 4, the two terminals of the LED 24 are connected to the battery 34 using a voltage divider which includes a potentiometer 70 for adjusting the current supplied to the LED. A second CdS light detector 72 is mounted on the side of the LED 24. The CdS detectors each have one terminal connected to a common line 74. Their other terminals are connected to terminals 76 and 78 respectively. The resistances of the CdS detectors are therefore measured between the terminal 76 and common and the terminal 78 and common.

Prior to making a measurement, the resistance of the detector 72 is measured and the potentiometer 70 is adjusted in order to bring the resistance of the detector 72 to a predetermined value. The resistance of the detector 28 is then measured. By adjusting the potentiometer 70 in this manner, potential variation in the intensity of the light emitted by the LED 24 due to change in temperature and component aging are avoided.

Teflon (registered trademark), which is hydrophobic, is commercially available in porous sheet form from MSI of Falls, N.Y. A simple and rugged cell for detecting water-immiscible organic liquids floating on the water table or percolating downwards through the unsaturated zone above the water table may therefore be made from a sheet of porous Teflon or hydrophobic filter paper interposed between a light source and a light detector. The water or organic liquid content versus capillary pressure/tension relationship of a hydrophilic or hydrophobic filter paper may be calibrated, and such filter paper may be used in detection cells for water and organic liquids respectively. These materials offer the advantage that the liquid content varies significantly with capillary pressure/tension.

The effect described herein can be used to measure the degree of saturation of biological tissues. In one experiment, a CdS light detector was placed on a laboratory bench directly beneath a fluorescent lighting fixture. A leaf that had just been removed from a tree was secured over the light detector. Initially, the leaf's petiol was immersed in a pool of water, and subsequently the petiol was removed from the water and the leaf was allowed to continue to transpire, so that its water content was reduced. It was found that the resistance of the detector increased somewhat relative to immediately before the petiol was removed from the water. The petiol was again immersed in the water, and the resistance of the detector decreased.

It will be appreciated that the invention is not restricted to the particular embodiments that have been described, and that variations may be made therein without departing from the scope of the invention as defined in the appended claims and equivalents thereof. For example, the invention is not limited to use of the particular materials that have been described. Also, the invention is not limited to the light source and light detector being attached to the porous body, since they may be optically coupled to the porous body by optical fibers.

We claim:

1. Apparatus for detecting a first of two immiscible liquids in the presence of the second liquid, comprising a translucent, porous, dimensionally stable body that absorbs the first liquid in preference to the second liquid, and means for detecting the amount by which light incident on the body is attenuated on propagation through the body.

2. Apparatus according to claim 1, further comprising a light source secured to the porous body.

3. Apparatus according to claim 1, for detecting an aqueous liquid, wherein the material of the porous body is hydrophilic.

4. Apparatus according to claim 3, wherein the hydrophilic material is fritted glass.

5. Apparatus according to claim 1, for detecting oil in the presence of water, wherein the material of the porous body is hydrophobic.

6. Apparatus according to claim 5, wherein the hydrophobic material is a porous synthetic polymer material.

7. Apparatus according to claim 1, wherein the material of the porous body is carried by support of cellulosic paper.

8. A method for detecting a first of two immiscible liquids in the presence of the second liquid, comprising providing a translucent, porous, dimensionally stable body that absorbs the first liquid in preference to the second liquid, placing the body in contact with a liquid medium that includes the second liquid, and detecting the amount by which light incident on the body is attenuated on propagation through the body.

9. A method according to claim 8, for detecting an aqueous liquid, wherein the material of the porous body is hydrophilic.

10. A method according to claim 8, for detecting oil, wherein the material of the porous body is hydrophobic.

11. A method according to claim 8, wherein the porous body has two opposite sides and the amount by which light incident on the body is attenuated on propagation through the body is detected by using a light detector at one side of the body and a light source at the opposite side of the body.

12. A method for detecting the degree to which a translucent, porous body of biological tissue is saturated with liquid, comprising the steps of illuminating the body and detecting the amount by which light is attenuated on propagation through the body.

13. Apparatus according to claim 6, wherein the hydrophobic material is fitted polyethylene.

14. A method for detecting first and second immiscible liquids in an absorbent and unsaturated body of solid material, comprising providing a translucent, porous body that absorbs the first liquid in preference to the second liquid and a second translucent, porous body that absorbs the second liquid in preference to the first liquid, placing the bodies in contact with the body of solid material, and detecting the amount by which light incident on the first and second bodies is attenuated on propagation through the bodies.

15. A method according to claim 14, wherein the first porous body is hydrophilic and the second porous body is hydrophobic.

16. A method according to claim 14, wherein the first and second bodies are dimensionally stable with respect to the direction of propagation of light through the bodies.

* * * * *

UNITED STATES PATENT AND TRADEMARK OFFICE
CERTIFICATE OF CORRECTION

PATENT NO. : 4,899,047

DATED : February 6, 1990

INVENTOR(S) : John W. Cary et al

It is certified that error appears in the above-identified patent and that said Letters Patent is hereby corrected as shown below:

On the cover sheet, left column, line 2, "Cry" should read --Cary--.

On the cover sheet, left column, in ICIREPAT [75], "Cry" should read --Cary--.

Column 6, line 30, delete "fitted" and substitute --fritted--.

Signed and Sealed this

Ninth Day of April, 1991

Attest:

HARRY F. MANBECK, JR.

Attesting Officer

Commissioner of Patents and Trademarks